(12) United States Patent
Penka et al.

(10) Patent No.: US 12,420,080 B2
(45) Date of Patent: Sep. 23, 2025

(54) HEART-LUNG MACHINE WITH SIMPLIFIED SETUP BASED ON ROLE-PROFILE MAPPING

(71) Applicant: LivaNova Deutschland GmbH, Munich (DE)

(72) Inventors: Ottmar Penka, Munich (DE); Friedemann Schubert, Munich (DE); Christian Hofstetter, Markt Indersdorf (DE)

(73) Assignee: LivaNova Deutschland GmbH, Munich (DE)

( * ) Notice: Subject to any disclaimer, the term of this patent is extended or adjusted under 35 U.S.C. 154(b) by 1130 days.

(21) Appl. No.: 17/322,375

(22) Filed: May 17, 2021

(65) Prior Publication Data

US 2021/0268260 A1    Sep. 2, 2021

Related U.S. Application Data

(63) Continuation of application No. PCT/EP2018/086320, filed on Dec. 20, 2018.

(51) Int. Cl.
*A61M 60/585*    (2021.01)
*A61M 1/36*    (2006.01)
(Continued)

(52) U.S. Cl.
CPC ........ *A61M 60/585* (2021.01); *A61M 1/3666* (2013.01); *A61M 60/113* (2021.01);
(Continued)

(58) Field of Classification Search
CPC ............... A61M 60/113; A61M 1/3666; A61M 60/515; A61M 60/585; A61M 2205/502; A61M 2209/084; A61M 2209/086; G06F 3/00; G06F 9/451; G06F 3/0481; G16H 40/40; G16H 40/63
See application file for complete search history.

(56) References Cited

U.S. PATENT DOCUMENTS

2002/0085952 A1*   7/2002  Ellingboe ........... A61M 1/3663
                                                         604/4.01
2002/0183585 A1*  12/2002  Willems .............. A61M 60/183
                                                           600/17

(Continued)

OTHER PUBLICATIONS

International Search Report and Written Opinion for International Application No. PCT/EP2018/086320 date of mailing Aug. 28, 2019.

*Primary Examiner* — Matthew Ell
*Assistant Examiner* — Alvaro R Calderon, IV
(74) *Attorney, Agent, or Firm* — Seager, Tufte & Wickhem LLP

(57) ABSTRACT

A heart lung machine (HLM) with simplified setup based on role-profile mapping. The HLM includes a control assembly including a control display device and a processing unit configured to create a mapping profile by associating each of a plurality of HLM component names with one of a plurality of HLM component roles and assigning at least one dependency between a first one of the plurality of HLM components and a second one of the HLM components. Each of the plurality of HLM component roles is associated with an HLM component function.

20 Claims, 5 Drawing Sheets

(51) Int. Cl.
  *A61M 60/113* (2021.01)
  *A61M 60/515* (2021.01)
  *G06F 3/00* (2006.01)
  *G06F 9/451* (2018.01)
  *G16H 40/40* (2018.01)
  *G16H 40/63* (2018.01)
  *G06F 3/0481* (2022.01)

(52) U.S. Cl.
  CPC ............ *A61M 60/515* (2021.01); *G06F 3/00* (2013.01); *G06F 9/451* (2018.02); *G16H 40/40* (2018.01); *G16H 40/63* (2018.01); *A61M 2205/502* (2013.01); *G06F 3/0481* (2013.01)

(56) References Cited

U.S. PATENT DOCUMENTS

| | | | |
|---|---|---|---|
| 2003/0013152 A1 | 1/2003 | Dejong | |
| 2007/0052683 A1* | 3/2007 | Knott | G06F 3/1446 345/173 |
| 2007/0253021 A1* | 11/2007 | Mehta | H04L 61/5038 382/128 |
| 2008/0065420 A1* | 3/2008 | Tirinato | G16H 10/60 705/3 |
| 2009/0054743 A1* | 2/2009 | Stewart | G16H 50/20 600/301 |
| 2009/0125840 A1* | 5/2009 | Squilla | G16H 40/20 715/810 |
| 2010/0238089 A1* | 9/2010 | Massand | G09G 5/14 345/1.1 |
| 2011/0001605 A1* | 1/2011 | Kiani | G16H 40/67 235/492 |
| 2012/0278759 A1* | 11/2012 | Curl | G16H 40/20 345/173 |
| 2014/0282181 A1* | 9/2014 | Declerck | A61M 1/02 715/771 |
| 2015/0070319 A1* | 3/2015 | Pryor | G06F 3/0425 345/175 |
| 2015/0301717 A1* | 10/2015 | Wekell | G06F 3/04842 715/835 |
| 2017/0102846 A1* | 4/2017 | Ebler | A61M 1/3623 |
| 2017/0372473 A1* | 12/2017 | Ujiie | G06F 3/0482 |
| 2018/0242926 A1* | 8/2018 | Muhsin | G16H 40/40 |
| 2019/0117070 A1* | 4/2019 | Muhsin | A61B 5/0295 |

* cited by examiner

HEART-LUNG MACHINE WITH SIMPLIFIED SETUP BASED ON ROLE-PROFILE MAPPING

CROSS REFERENCE TO RELATED APPLICATIONS

This application is a continuation of International Application No. PCT/EP2018/086320, filed Dec. 20, 2018, the disclosure of which is incorporated herein by reference.

TECHNICAL FIELD

The present disclosure relates to a mapping system for medical equipment, in particular, a mapping system for connected components of heart lung machines (HLMs).

BACKGROUND

HLMs typically includes a number of different dependencies between different components of the HLM. The setup of HLMs traditionally involved a large amount of abstraction and mental work from the individual performing the setup, as well as a large amount of user input to the system. Thus, to set up HLMs, users traditionally had to memorize frequently used dependencies, establish mapping of control signals between connected HLM components and actuator control units (ACUs), and/or the like. This process was burdensome and made it difficult for users to set up HLMs and have an overview of the various dependencies in mind.

SUMMARY

It is provided a heart lung machine (HLM), comprising: an HLM base and a plurality of component connectors coupled to the HLM base and configured to facilitate removably connecting an HLM component to the base, the HLM comprising: an HLM base; a plurality of HLM component connectors coupled to the HLM base, wherein each of the plurality of HLM component connectors is configured to facilitate removably connecting an HLM component to the HLM base; a control assembly comprising a control display device and a processing unit, the processing unit configured to create a mapping profile by: associating each of a plurality of HLM component names with one of a plurality of HLM component roles, wherein each of the plurality of HLM component roles is associated with an HLM component function; assigning at least one dependency between a first one of the plurality of HLM components and a second one of the HLM components, the at least one dependency comprising at least one of an interaction, an interaction protocol, and a rule; providing an HLM system mapping user interface (Ul) on a display device, the HLM system mapping Ul comprising a plurality of HLM component connector representations, each of the HLM component connector representations corresponding to an HLM component connector; receiving an indication of a user selection of an HLM component connector representation of the plurality of HLM component connector representations, the HLM component connectors representation corresponding to a HLM component connector, wherein the HLM component connector is configured to facilitate connecting an HLM component to the HLM base; providing a HLM component connection mapping interface, the HLM component connection mapping interface corresponding to the HLM component connector; receiving, via the HLM component connection mapping interface, a user input assigning an HLM component name to the HLM component; and associating, in response to receiving the user input, the HLM component name with the HLM component, thereby instantiating the at least one dependency. Furthermore, it is provided a method of using a heart lung machine (HLM), the HLM comprising an HLM base and a plurality of component connectors coupled to the HLM base and configured to facilitate removably connecting an HLM component to the base, the method comprising: associating each of a plurality of HLM component names with one of a plurality of HLM component roles, wherein each of the plurality of HLM component roles is associated with an HLM component function; assigning at least one dependency between a first one of the plurality of HLM components and a second one of the HLM components, the at least one dependency comprising at least one of an interaction, an interaction protocol, and a rule; receiving an indication of a system mapping trigger event; providing, in response to receiving the indication of the system mapping trigger event, an HLM system mapping user interface (Ul) on a display device, the HLM system mapping Ul comprising a plurality of HLM component connector representations, each of the HLM component connector representations corresponding to an HLM component connector; receiving an indication of a user selection of a first HLM component connector representation, the first HLM component connector representation corresponding to a first HLM component connector, wherein the first HLM component connector is configured to facilitate connecting a first HLM component to the HLM base; providing a first HLM component connector mapping interface, the first HLM component connector mapping interface corresponding to the first HLM component connector; receiving, via the first HLM component connector mapping interface, a user input assigning a first HLM component name to the first HLM component connector; associating, in response to receiving the user input, the first HLM component name with the first HLM component; receiving an indication of a user selection of a second HLM component connector representation, the second HLM component connector representation corresponding to a second HLM component connector, wherein the second HLM component connector is configured to facilitate connecting a second HLM component to the HLM base; providing a second HLM component connector mapping interface, the second HLM component connector mapping interface corresponding to the second HLM component connector; receiving, via the second HLM component connector mapping interface, a user input assigning a second HLM component name to the second HLM component connector; and associating, in response to receiving the user input, the second HLM component name with the second HLM component.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1A:
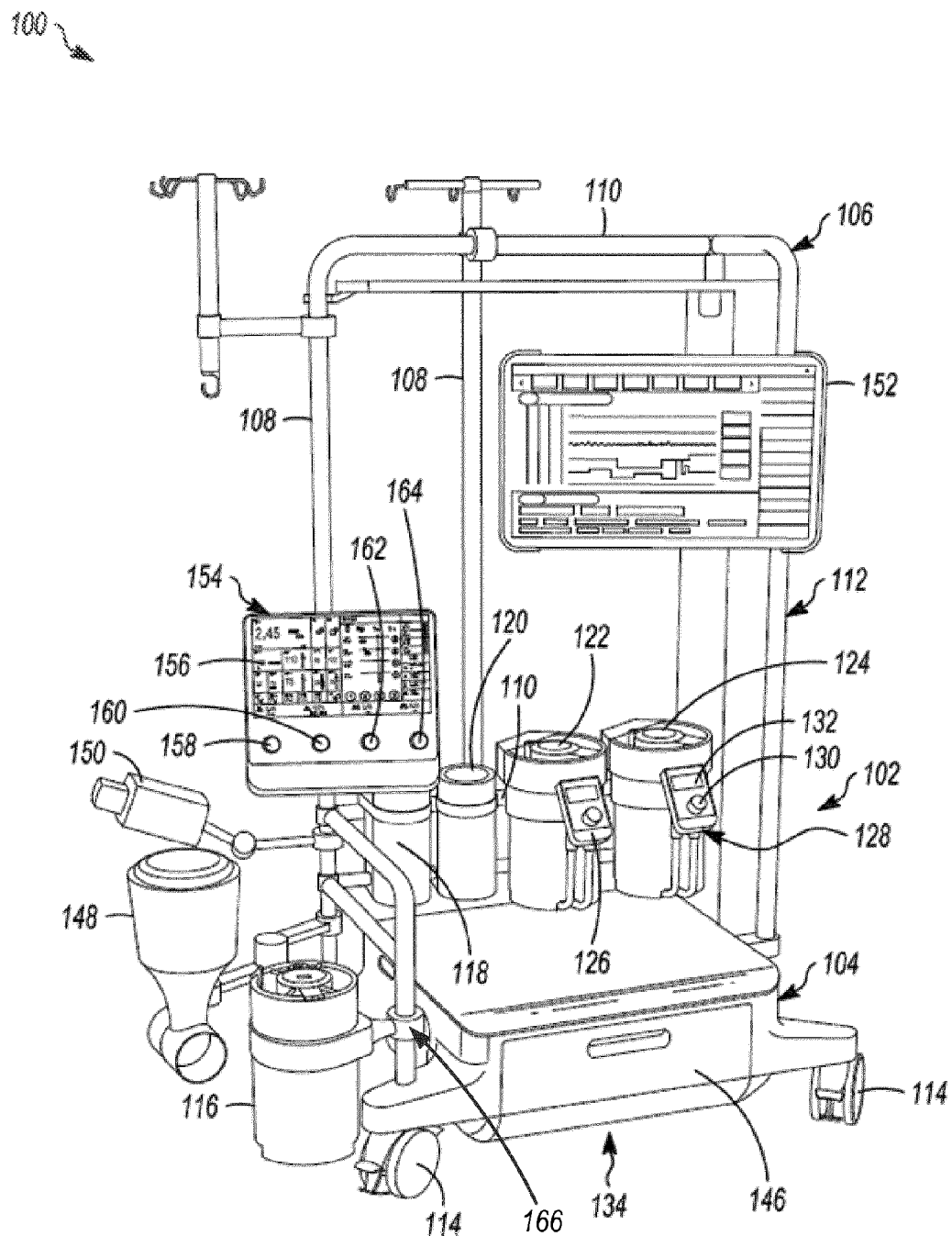
FIG. 1A is a front perspective view of an illustrative heart lung machine (HLM), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The terms "up," "upper," and "upward," and variations thereof, are used throughout this disclosure for the sole purpose of clarity of description and are only intended to refer to a relative direction (i.e., a certain direction that is to be distinguished from another direction), and are not meant to be interpreted to mean an absolute direction. Similarly, the terms "down," "lower," and "downward," and variations thereof, are used throughout this disclosure for the sole purpose of clarity of description and are only intended to refer to a relative direction that is at least approximately opposite a direction referred to by one or more of the terms "up," "upper," and "upward," and variations thereof.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Figure 1B:
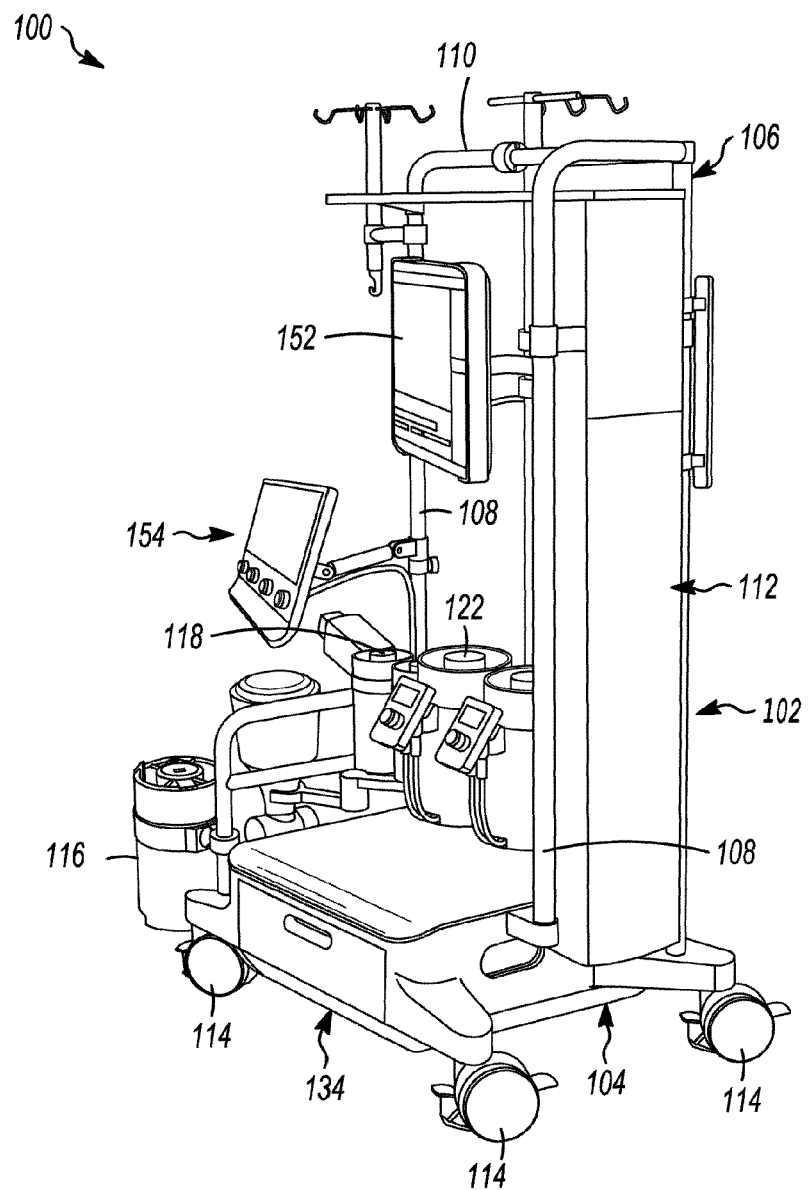
FIG. 1B is a side perspective view of the illustrative HLM depicted in FIG. 1A, in accordance with embodiments of the subject matter disclosed herein.

FIG. 1A is a front perspective view of an illustrative heart lung machine (HLM) 100, in accordance with embodiments of the subject matter disclosed herein; and FIG. 1B is a side perspective view of the illustrative HLM 100 depicted in FIG. 1A, in accordance with embodiments of the subject matter disclosed herein. As shown, the HLM 100 includes a trolley 102 having a base 104 that includes an internal cavity (not shown) for housing any number of different controls, electrical circuits, hydraulic circuits, a battery discharger, and/or the like. For example, in embodiments, a peripheral processing unit may be disposed within the base 104. A mast assembly 106 is coupled to the base 104 and extends upwards from the base 104. The mast assembly 106 may include any number of different mast components, including vertical poles 108, horizontal rails 110, and/or the like. In embodiments, the trolley 102 includes an enclosure 112 that is configured to facilitate cable management, provide A/C outlets, include a power switch for the HLM 100, include an extension box, and/or the like. As shown, the trolley 102 also may include wheels 114 coupled to the base 104.

As shown, the HLM 100 also may include a number of different types of components such as an oxygenator 115 (which may actually be considered to be an element of an extracorporeal circuit used with the HLM, but may be referred to herein as being a component of the HLM due to being connected to the trolley 102); pumps 116, 118, 120, 122, 124; and/or the like. In embodiments, one or more of the components 115, 116, 118, 120, 122, and 124 (and/or others) may be coupled to any number of different portions of the mast assembly 106, and may include, for example, an exposed actuator control unit (ACU). For example, as shown, pumps 122 and 124 may each include an exposed ACU 126 and 128, operably connected thereto, respectively. As shown, an ACU 128 may include a control knob 130 configured to receive user input (e.g., manipulation of the knob 130) for controlling operation of the pump 124, and an information display device 132 configured to present information associated with the pump such as, for example, one or more parameters (e.g., measured device parameters such as, for instance, flow, rpm, etc.). According to embodiments, an ACU may be configured to facilitate control of a pump, a motorized clamp, a motorized occluder, an infusion device, and/or any number of other types of devices that may be associated with an HLM.

Traditionally, HLMs have utilized roller pumps that are each integrated into a modular console component. The modular console components are stacked next to one another on the base of an HLM to provide an array of pumps. The modular console component also houses an ACU having an interface for controlling the corresponding integrated roller pump. One advantage of having the ACU interface provided at the modular console component is that, during an emergency situation, the perfusionist can easily determine the ACU that corresponds to a particular roller pump. More recently, mast mounted roller pumps (without the modular console component housing) have been utilized in HLMs. Mast mounted pumps provide more flexibility in the configuration of the HLM; however, if the ACUs for the mast mounted pumps are located remotely, or detached from, the mast mounted pumps, it's potentially more difficult for the perfusionist to identify the ACU that controls a particular pump.

Embodiments of the present disclosure include mast mounted roller pumps, such as pumps 122 and 124 of FIG. 1A, having corresponding ACUs, such as ACUs 126 and 128, respectively. The ACUs 126 and 128 are attached, connected, or otherwise operatively coupled to the corresponding mast mounted roller pumps 122 and 124. The connectedness, or close proximity of the ACU to the mast mounted roller pump allows the user to precisely determine the ACU that controls a particular mast mounted roller pump in a high pressure, or emergency situation, including a situation where the control display device 156 is not functioning properly or is disabled. Thus, the ability to mount the pumps 122 and 124 to the mast assembly 106 allows a much wider range of configurations to meet the user's particular needs.

Figure 1C:
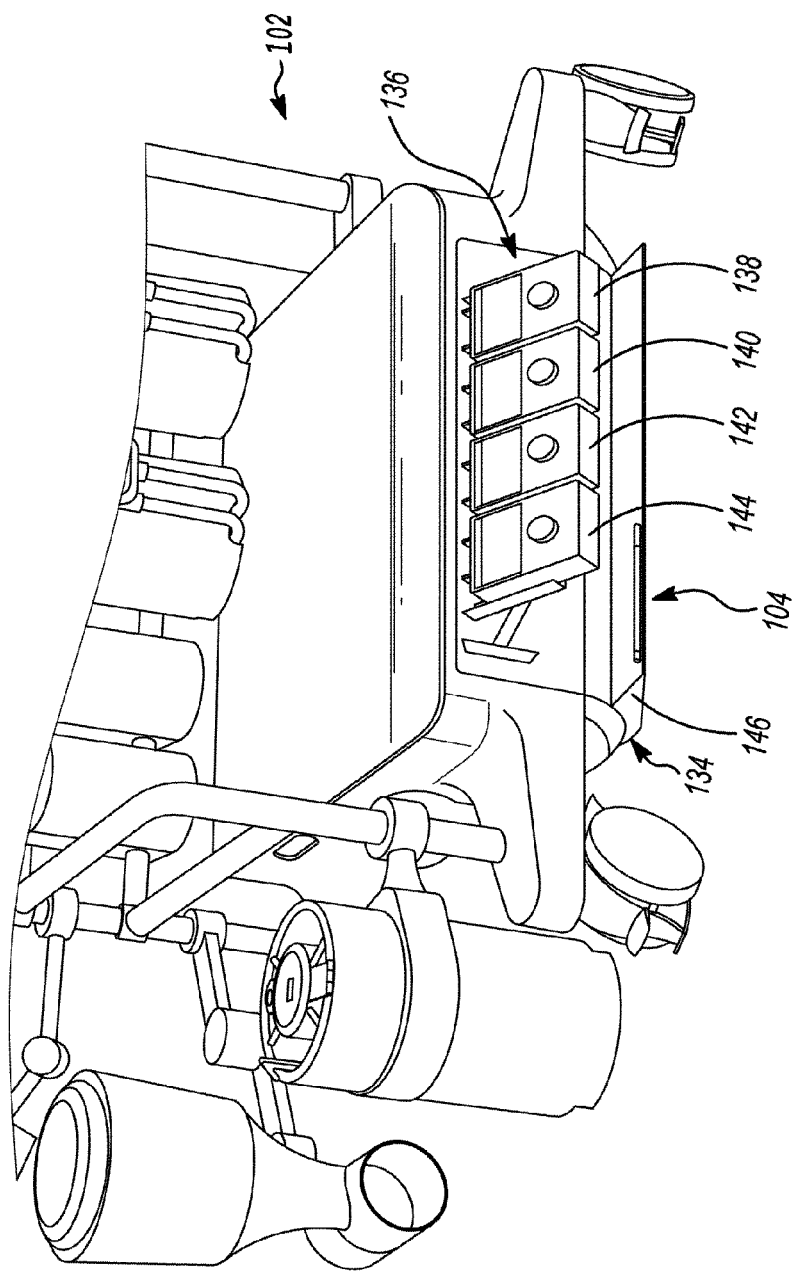
FIG. 1C is a partial perspective view of the base of the trolley depicted in FIGS. 1A and 1B, in accordance with embodiments of the subject matter disclosed herein.

FIG. 1C is a partial perspective view of the base 104 of the trolley 102 depicted in FIGS. 1A and 1B, in accordance with embodiments of the subject matter disclosed herein. As shown in FIG. 1C, the base 104 of the trolley 102 may include a lower housing 134 having an enclosure 136 configured to house one or more ACUs 138, 140, 142, and 144. In embodiments, any number of ACUs may be disposed in the enclosure 136. For example, in embodiments, all of the ACUs for actuators associated with the HLM 100 may be disposed at least partly in the enclosure 136. In embodiments, one or more ACUs may be exposed by being disposed directly on or near the corresponding actuators. According to embodiments, the enclosure 136 may be configured to be closed to protect the ACUs disposed therein, or opened to reveal the ACUs. For example, the lower housing 134 may include a drawer, cabinet, and/or the like. As shown, in embodiments, the lower housing 134 may include a door 146 configured to be opened and closed to selectively expose or conceal the enclosure 136. Each of the ACUs 138, 140, 142, and 144 may be operably connected to a corresponding one of the components 116, 118, 120, 122 (e.g., in cases in which the pump 122 does not include an exposed ACU 126), or 124 (e.g., in cases in which the pump 124 does not include an exposed ACU 128) and/or other actuators.

As is further shown in FIGS. 1A and 1B, the HLM 100 may include any number of other components such as, for example, a venous reservoir 148 (which may be, for example, a component of an extracorporeal circuit that may be used in combination with the HLM 100), an electronic venous occluder (EVO) 150, a peripheral display device 152, a control assembly 154, any number of various types of sensors, and/or the like. According to embodiments, any number of the components discussed herein, others not discussed herein, or aspects of the components (e.g., sensors and/or actuators associated with components) may be operably connected to the peripheral processing unit (not shown), which may be configured to receive parameter data from any one or more of the components, process parameter data, receive control signals from any one or more input devices (e.g., ACU control knobs 130, etc.), provide control signals to any one or more of the components, and/or the like.

In embodiments, the peripheral display device 152 may be operably connected to the peripheral processing unit and configured to present a set of parameter data received from the peripheral processing unit. In embodiments, the peripheral display device 152 may be, include, or be included within a data recording and/or management system. That is, for example, the peripheral display device 152 may include, or be otherwise associated with, a processing unit separate from that of the HLM, and/or may be configured to record and/or display any number of different operative HLM parameters. In some implementations, for example, the peripheral display device 152 may be configured to obtain and record all of the operative HLM parameter values and/or patient parameters provided by any number of additional monitoring devices. The peripheral display device 152 may be configured to present, graphically, representations of any number of the obtained parameter values, changes in parameter values over time, derived parameter values (e.g., values derived from parameter values), and/or the like.

During an operation, the primary focus of a user of the HLM 100 generally is the oxygenator 115 and the venous reservoir 148. Accordingly, embodiments of the subject matter disclosed herein provide a control assembly 154 near those two components 115 and 148 so that the user can access control devices and view displayed parameters without having to move away from, or be distracted from, the oxygenator 115 and venous reservoir 148. According to embodiments, the control assembly 154 may include a control display device 156 and a number of input control devices 158, 160, 162, and 164. In embodiments, the control assembly 154 may include any number of input control devices (e.g., 1, 2, 3, 4, 5, 6, etc.) and the number of input control devices may be less than or equal to the number of ACUs in the enclosure 136. The control display device 156 may be configured to present a subset of the parameters presented by the peripheral display device 152 and/or the peripheral display device 152 may be configured to present a subset of the subset of parameters presented by the control display device 156. A different subset of the set of parameter data may be displayed by the peripheral display device 152. In embodiments, the peripheral display device 152 may be configured to display real-time waveform traces, while the control display device 156 may be configured to display numerical representations of the same and/or different parameters.

That is, for example, regardless of what is displayed on the peripheral display device 152, the control display device 156 may be configured to display a specified subset of parameter data that is particularly useful and/or important with respect to a procedure being performed. That specified subset of parameter data may be predetermined, based on the type of procedure; dynamically presented, based on a status of the patient and/or device; and/or the like. In embodiments, all of the information configured to be presented on the control display device 156 may be presented simultaneously-that is, without having tabs for accessing screens showing additional information, without requiring menus for accessing screens showing additional information during a procedure, and/or the like. In embodiments, the control display device 156 may include selectable representations presented onscreen that can be used to configure the display such as, for example, by enabling a user to select a display mode corresponding to a particular HLM component (e.g., a centrifugal pump, a roller pump, etc.), to select a particular display module (e.g., a pre-configured set of data fields in a particular arrangement), and/or the like.

According to embodiments, the peripheral display device 152 and/or the control display device 156 may include an input mechanism configured to enable user interaction with one or more features displayed on the display device 152 and/or 156. That is, for example, the peripheral display device 152 and/or the control display device 156 may be, or include, a touchscreen device configured to receive user input. In embodiments, the peripheral display device 152 and/or the control display device 156 may include an input device connected thereto such as, for example, a mouse, a trackpad, a joystick, and/or the like.

According to embodiments, for example, additional data from devices external to the HLM (e.g., blood gas monitors, electrocardiogramtilators, patient monitors, etc.) may be displayed on the peripheral display device 152. As indicated above, the peripheral display device 152 may be controlled by a peripheral processing unit that is separate from the central system unit of the HLM. The peripheral processing unit associated with the peripheral display device 152 may be configured to obtain parameter values (e.g., from the central system unit, sensors, actuators, external devices, etc.) and may be configured to collect the data in a database. The peripheral processing unit may be communicatively coupled to the peripheral display device 152, HLM components, and/or external devices. In embodiments, while the peripheral processing unit may be configured to receive data from the central system unit, an interface unit or any other communication port embedded in the HLM, the peripheral processing unit may be configured so as to not send any data to the central system unit, to the interface unit or other communication ports of the HLM. In other embodiments, the peripheral processing unit, the central system unit, the interface unit or any other communication port of the HLM may be configured to exchange data with one another and/or other devices. According to embodiments, a user may select which data is to be stored by which processing or system unit.

The peripheral processing unit associated with the peripheral display device may be configured to allow user interaction therewith, generate reports based on the obtained data, generate printable documents corresponding to a medical procedure, interact with a printer to cause the printer to print such reports, and/or the like. In embodiments, the peripheral processing unit may be configured to generate, and cause the peripheral display device to present, graphs (e.g., trend charts, curves, etc.) and/or other visual representations of any number of various aspects of data received from HLM components and/or external devices. In embodiments the peripheral display device may be configurable such that a user can select certain types of data and/or representations thereof to display, the manner in which it is displayed, and/or the like. In contrast, for example, the control display device 156 may include only limited configurability, if at all. In this manner, the control display device 156 can be relied upon to present representations of data relevant to the HLM's current use. According to other embodiments, the control display device 156 may have any amount of configurability.

In embodiments, each of the input control devices 158, 160, 162, and 164 may be operably connected to one of the actuators and may be configured to receive user input for controlling an operation of the actuator. According to embodiments, the input control devices 158, 160, 162, and 164 may be operably connected to the respective ACUs 138, 140, 142, and 144, in which case, the input control devices 158, 160, 162, and 164 act in parallel to the ACUs, but do not have priority over them in controlling the actuators. In embodiments, the input control devices are directly connected to the respective ACUs, and the ACUs are connected to the respective actuators, such that an actuator can be controlled by an input control device only through an ACU or directly by an ACU. Therefore, the ACU has prevalence over the input control device in controlling the actuator.

As is further shown in FIG. 1A, the HLM 100 may include a connection assembly 166 configured to facilitate connecting at least one HLM component to the HLM base 104. The connection assembly 166 may include any number of different HLM component connectors configured to facilitate removably connecting an HLM component to the HLM base 104. Each HLM component connector may include any number of connection elements configured to facilitate operatively connecting an HLM component to other components of the HLM. In embodiments, the connection elements may include fluid connection elements, energy connection elements, and/or data connection elements. In embodiments, the control assembly 154 may be configured to facilitate configuring the connection assembly 166. According to embodiments, configuring the connection assembly 166 may include, for example, providing input to a control unit via the control assembly 154 that assigns a particular type of HLM component to the connection assembly 166 and/or a connector thereof, assigns a particular HLM component to the connection assembly 166 and/or a connector thereof, causes the control assembly to display a representation of the connector and/or HLM component, causes the control assembly to include data received via the connector to be displayed in a user interface, and/or the like.

For example, an HLM system typically includes a number of different dependencies between different components of the HLM. In the context of the discussion herein, a dependency between two HLM components is any type of functional link, rule, relationship, and/or the like in which an action and/or change of state of one HLM component triggers or otherwise causes an action and/or change of state of the other HLM component. In embodiments, dependencies may include interventions, stop links, master/slave relationships, and/or the like. An intervention may include, for example, a configuration in which the bubble detector controls the arterial pump in such way that the pump is being stopped automatically when air is detected in the line. A stop link may include, for example, a configuration in which the blood cardioplegia pump is linked to the arterial pump in such way that the cardioplegia pump is slowed down (or even stopped) when the arterial pump is slowed down or stopped. A master/slave relationship may include, for example, for blood cardioplegia, a configuration in which both cardioplegia pumps are linked in such way that both pumps always deliver flow according to a predefined ratio.

Any number of other dependencies, types of dependencies, and/or the like may be contemplated in accordance with embodiments of the subject matter disclosed herein. The setup of HLMs (e.g., assigning actuator control units (ACUs) to HLM components, assigning control devices to ACUs, configuring dependencies, and/or the like) traditionally involved a large amount of abstraction and mental work from the individual performing the setup, as well as a large amount of user input to the system. Thus, to set up HLMs, users traditionally had to memorize frequently used dependencies, establish mapping of control signals between connected HLM components and ACUs in distributed menus, and/or the like. This process was burdensome and made it difficult for users to intuitively set up HLMs for use.

Embodiments of the subject matter disclosed herein may facilitate a faster, more intuitive and more automated way of setting up HLMs, thereby providing a solution to the well-known technical problem in HLMs outlined above, by providing an intuitive, user-friendly interface for quickly setting up an HLM for use. Thus, embodiments of the subject matter disclosed herein provide, for the first time, an ability to rapidly connect HLM components to an HLM base and set up the HLM for use in an urgent operation, thereby improving the effectiveness of HLMs as support tools for such operations. For example, by establishing functional roles of HLM components within the system prior to connecting any HLM components, establishing dependencies between HLM components prior to connecting any HLM components, and associating pre-established HLM component names with the established roles, a user of the system may be able to simply connect an HLM component to an HLM component connector and assign a predefined name to the HLM connector and, thus, to the HLM component. Upon assignment of the HLM component name to the HLM component, the system may automatically configure the HLM component such as, for example, by associating a functional role with the HLM component, associating any corresponding established dependencies with the HLM component, and/or the like. In embodiments, the HLM component names may be selected from a list of predefined names such that the user also need not input any individual names. In this manner, for example, set up may be accomplished by simply connecting the HLM components and clicking buttons on the Ul to select the appropriate names and/or other characteristics, reducing the time the user must take to functionally incorporate an HLM component with the HLM.

According to embodiments, any one or more of the components of the illustrative HLM 100 may be implemented on one or more computing devices. A computing device may include any type of computing device suitable for implementing aspects of embodiments of the disclosed subject matter. Examples of computing devices include specialized computing devices or general-purpose computing devices such "control units," "control assemblies," "workstations," "servers," "hand-held devices," "heart lung machines," "controllers," and the like, all of which are contemplated within the scope of FIG. 1, with reference to various components of the HLM 100.

In embodiments, a computing device includes a bus that, directly and/or indirectly, couples the following devices: a processing unit, a memory, an input/output (I/O) port, an I/O component, and a power supply. Any number of additional components, different components, and/or combinations of components may also be included in the computing device. The I/O component may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus represents what may be one or more busses (such as, for example, an address bus, data bus, or combination thereof). Similarly, in embodiments, the computing device may include a number of processing units, a number of memory components, a number of I/O ports, a number of I/O components, and/or a number of power supplies. Additionally any number of these components, or combinations thereof, may be distributed and/or duplicated across a number of computing devices.

In embodiments, the memory includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory stores computer-executable instructions for causing the processor to implement aspects of embodiments of system components discussed herein and/or to perform aspects of embodiments of methods and procedures discussed herein.

The computer-executable instructions may include, for example, computer code, machine-useable instructions, and the like such as, for example, program components capable of being executed by one or more processors associated with the computing device. Program components may be programmed using any number of different programming environments, including various languages, development kits, frameworks, and/or the like. Some or all of the functionality contemplated herein may also, or alternatively, be implemented in hardware and/or firmware.

The illustrative HLM 100 shown in FIGS. 1A-1C is not intended to suggest any limitation as to the scope of use or functionality of embodiments of the present disclosure. The illustrative HLM 100 also should not be interpreted as having any dependency or requirement related to any single component or combination of components illustrated therein. Additionally, various components depicted in FIGS. 1 A-1C may be, in embodiments, integrated with various ones of the other components depicted therein (and/or components not illustrated), all of which are considered to be within the ambit of the present disclosure.

Figure 2:
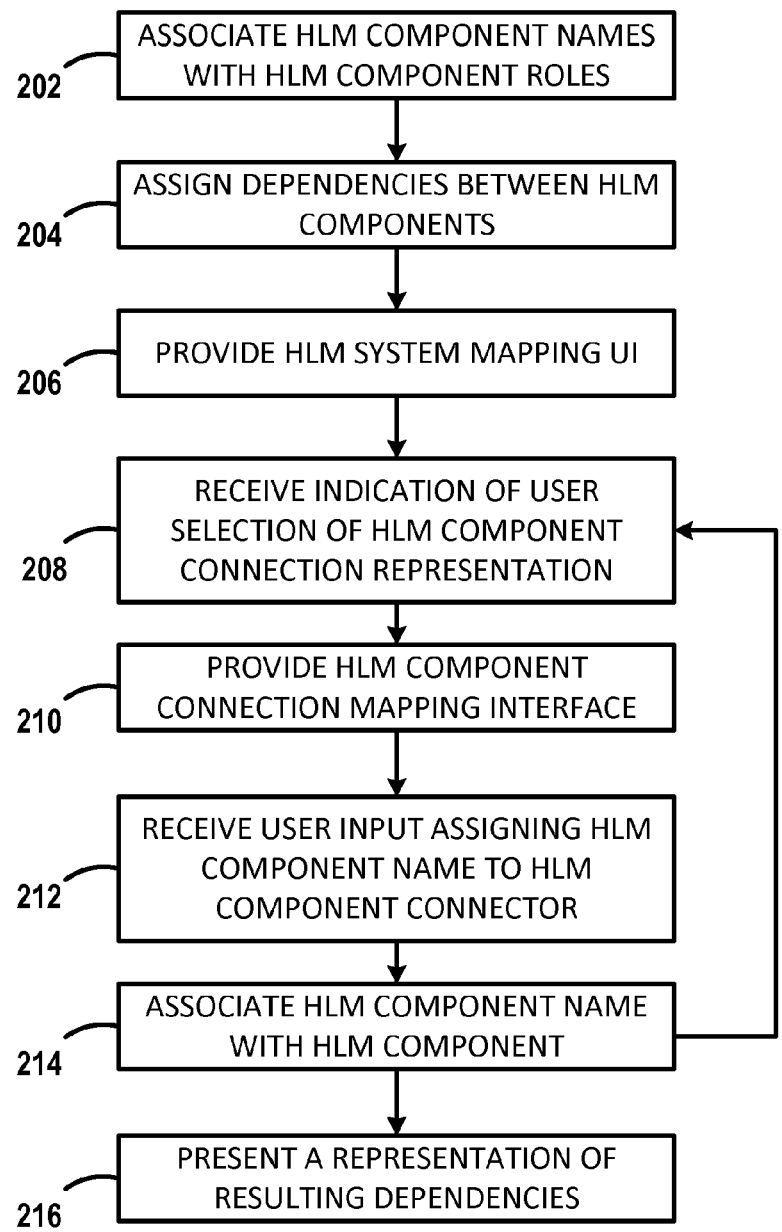
FIG. 2 is a flow diagram depicting an illustrative method of using an HLM, in accordance with embodiments of the subject matter disclosed herein.

FIG. 2 is a flow diagram depicting an illustrative method 200 of using a heart lung machine (HLM). According to embodiments, the HLM may be, or be similar to, the HLM 100 depicted in FIGS. 1A-1C. According to embodiments, for example, the HLM may include an HLM base and a number of component connectors coupled to the HLM base, each connector being configured to facilitate removably connecting an HLM component to the base.

According to embodiments, the method 200 may include associating each of a number of HLM component names with one of a number of HLM component roles, where each of the plurality of HLM component roles defines an HLM component function (block 202). For example, the association between the HLM component names and roles may be performed and/or otherwise established in computer code (e.g., as part of an algorithm performable by a processing device). The method 200 may further include assigning at least one dependency between a first one of the HLM components and a second one of the HLM components, the at least one dependency including at least one of an interaction, an interaction protocol, and a rule (block 204). In embodiments, an interaction may include a configuration in which one HLM component communicates with, shares data with, and/or otherwise interacts with (in one or both directions) another HLM component. An interaction protocol may include any number of different communication protocols, interaction algorithms, and/or the like that specify some aspect of how an interaction between two HLM components is to take place. According to embodiments, a rule may include at least one of an intervention, a stop link, and a master/slave relationship, as explained herein.

Embodiments of the method 200 further include providing an HLM system mapping user interface (Ul) on a display device (block 206). In embodiments, the HLM system mapping Ul may include a plurality of HLM component connector representations, each of the HLM component connector representations corresponding to an HLM component connector. In embodiments, the HLM system mapping Ul may be provided in response to receiving the indication of the system mapping trigger event. A system mapping trigger event may include, for example, detection of connection of an HLM component to a HLM component connector, receipt of user input directing the system to provide the HLM system mapping Ul, and/or the like. That is, for example, the trigger event may be the instantiation of a mapping user interface. Upon instantiation of the mapping user interface, the HLM components connected at the time may be scanned (e.g., via a CAN bus) and mapped to create a profile. In embodiments, during the process of mapping (e.g., assigning names and preferences), the system may recognize connection of new HLM components, but will not necessarily incorporate those newly connected HLM components in the profile.

In embodiments, the method 200 may further include receiving an indication of a user selection of a first HLM component connector representation (block 208). The first HLM component connector representation may correspond, for example, to a first HLM component connector, where the first HLM component connector is configured to facilitate connecting a first HLM component to the HLM base. Embodiments of the method 200 further include providing, in response to receiving the indication of the user selection of the first HLM component connector representation, a first HLM component connector mapping interface (block 210), the first HLM component connector mapping interface corresponding to the first HLM component connector. According to embodiments, the HLM component connector may be of a common type and a portion of software contained in the associated Actuator Control Unit (ACU) may be configured to detect the type of HLM component that is connected to the HLM component connector. In this manner, the ACU may be configured to control the actuator of the connected HLM component. In embodiments, the first HLM component connector may include, for example, a clamp connector configured to facilitate connecting a clamp to the HLM base or a pump connector configured to facilitate connecting a pump to the HLM base.

In embodiments, the method 200 may further include receiving, via the first HLM component connector mapping interface, a user input assigning a first HLM component name to the first HLM component connector (block 212); and associating, in response to receiving the user input, the first HLM component name with the first HLM component (block 214). In embodiments, for example, the method 200 may include associating the first HLM component connector with a first actuator control unit (ACU), thereby configuring the first ACU to facilitate controlling the first HLM component. Embodiments of the method 200 may further include presenting, on the display device, a representation of the at least one dependency (block 216). Additionally, or alternatively, representations of HLM component roles, names, control mappings, and/or the like, may be presented on the display device. For example, the processing unit may be further configured to provide a name list comprising a first HLM component name, where the processing unit populates the name list with the first HLM component name based on a control functionality of an actuator control unit (ACU), and where the ACU determines the control functionality by detecting an actuator type of the connected HLM component.

As shown in FIG. 2, embodiments of the steps 208-214 may be repeated for any number of additional HLM components. That is, for example, in another iteration of the steps, the method 200 may include receiving an indication of a user selection of a second HLM component connector representation, the second HLM component connector representation corresponding to a second HLM component connector, where the second HLM component connector is configured to facilitate connecting a second HLM component to the HLM base; providing a second HLM component connector mapping interface, the second HLM component connector mapping interface corresponding to the second HLM component connector; receiving, via the second HLM component connector mapping interface, a user input assigning a second HLM component name to the second HLM component connector; and associating, in response to receiving the user input, the second HLM component name with the second HLM component. In embodiments, for example, the HLM component connector mapping interfaces may be, or include, pop-up windows associated with the mapping interface.

According to embodiments, a user may assign the same name to two different HLM components initially. For example, embodiments of the method 200 may include associating the second HLM component connector with a second actuator control unit (ACU), thereby configuring the second ACU to facilitate controlling the second HLM component; and determining that the first HLM component name and the second HLM component name are identical. To maintain mapping consistency and differentiation throughout the system, the processing unit may be configured to assign a modifier to the name of the second HLM component name so that the second HLM component name is different that the first HLM component name. In embodiments, the modifier may include any sort of designation that differentiates the second name from the first, and, in embodiments, may be descriptive of the functional role of the associated HLM component.

Additionally or alternatively, embodiments may include virtual HLM components (and/or component channels/connectors). A virtual component and/or connector may be a representation of a calculation based on one or more pieces of data obtained and/or generated by one or more other HLM components. For example, in embodiments, the first HLM component connector may include a first Sensor Interface Unit (SIU) configured to facilitate connecting a first sensor probe to the HLM base (e.g., a pressure sensor probe, a temperature sensor probe, etc.), and the second HLM component connector may include a second SIU configured to facilitate connecting a second sensor probe to the HLM base. In embodiments, the method 200 may further include associating, in response to a first user input, a first sensor name with the first SIU; associating, in response to a second user input, a second sensor name with a second sensor SIU; and associating a virtual sensor name with a virtual sensor SIU. The virtual sensor may represent a relationship between the first sensor SIU and the second sensor SIU. For example, in embodiments, the virtual sensor may include a channel that results in a calculated value being displayed on the display device such as, for example, a differential pressure, a differential temperature, an average pressure, an average temperature, and/or the like.

Figure 3:
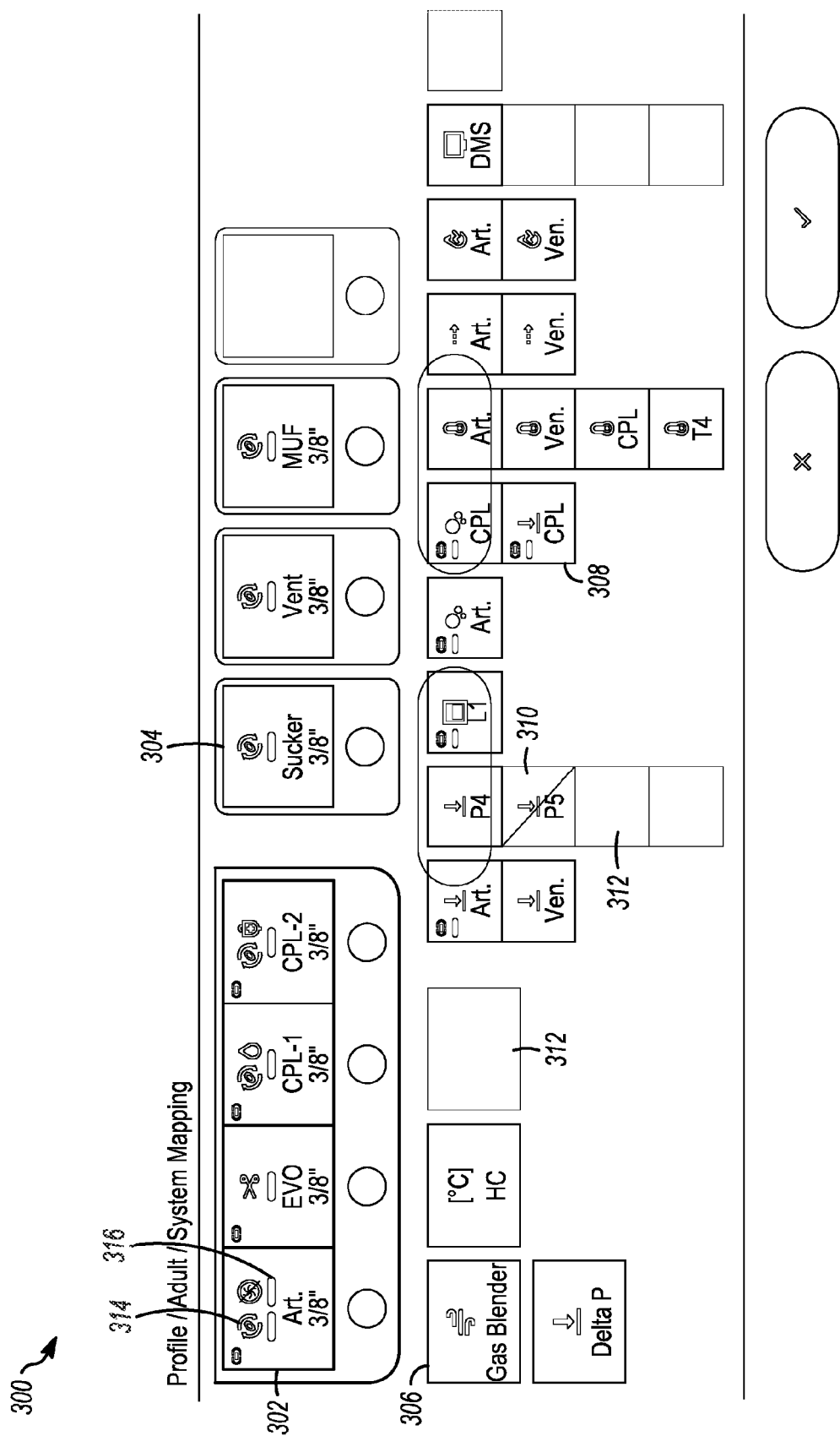
FIG. 3 is a screen shot depicting an HLM system mapping user interface (UI), in accordance with embodiments of the subject matter disclosed herein.

FIG. 3 is a screenshot depicting an illustrative HLM system mapping user interface (Ul) 300 in accordance with embodiments of the subject matter disclosed herein. As shown, the Ul 300 includes a number of HLM component connector representations 302, 304, 306, and 308, each of the HLM component connector representations corresponding to an HLM component connector. As shown, in embodiments, an HLM component connector representation 310 corresponding to an HLM component connector to which an HLM component has been connected but that has been switched off by the user during the mapping process may include an indication that indicates that the HLM component connected is switched off (e.g., a diagonal line through the representation, faded lines, and/or the like). In embodiments, the representation 310 may include an indication to indicate that, although an HLM component is connected to the corresponding HLM component connector, that HLM component is offline or otherwise not communicating with the control panel. In such embodiments, for example, a blank space 312 may be used to indicate an HLM component connector that does not have an HLM component connected to it.

In operation, a control assembly of an HLM may include a Settings Menu screen from which a user may select a profile (e.g., by tapping a profile button). For example, in embodiments, the control assembly processing unit may be configured to maintain, in memory, a number of different configuration profiles. Each profile may include a configuration of HLM component connector assignments, functional role assignments, dependencies, and/or the like. In embodiments, for example, a user may be able to save a profile associated with a particular procedure, patient, and/or the like. In embodiments, the Settings Menu may include a selectable button for a default profile, a selectable button for a new profile, and a selectable button for an existing profile. Upon receiving an indication of a selection of one of the profile buttons, the processing unit may be configured to present a Profile Setup Menu, which may present any number of different options for setting up a profile, editing a profile, and/or the like.

One of the options presented in the Profile Setup Menu (or a Settings Menu, or other Ul) may be a selectable option (e.g., a Map System button) for causing the processing unit to provide the HLM system mapping Ul 300. Upon detecting an occurrence of a system mapping trigger event (e.g., receiving an indication that user has provided an input to the processing unit to invoke the HLM system mapping Ul, detecting a new connection of an HLM component to an HLM component connector, etc.), the processing unit provides, via a display device, the HLM system mapping Ul 300. The HLM system mapping Ul 300 may, in embodiments, be configured to present, upon being instantiated, a previous mapping configuration, a new mapping configuration, and/or the like. As shown, the HLM system mapping Ul 300 may include an HLM component connector representation 302, 304, 306, 308, 310, 312 for each HLM component connector associated with the HLM. When an HLM component is connected to one of the HLM component connectors, the representation may, for example, be modified to include a representation of the type of HLM component connected, a set of selectable options for setting properties for the type of HLM component connected, and/or the like.

In response to receiving a user selection of an HLM component connector representation 302 corresponding to a pump connector, the processing unit may provide an HLM component connection mapping interface that may be configured to facilitate configuration of the corresponding HLM component connector. For example, the HLM component connection mapping interface may be configured to receive a user input assigning an HLM component name to the HLM component (e.g., via the HLM component connector). Other settings that may be configured may include, for example, the type of pump (e.g., roller or centrifugal), an identification color (e.g., a color that can be used on various parts of the HLM corresponding to that HLM component to identify that the various parts are associated with that HLM component), a direction of rotation (for roller pumps), a tubing size (for roller pumps), whether the HLM component is disabled/enabled, and/or the like. In response to receiving the user input, the processing unit may be configured to associate the HLM component name with the HLM component and/or the HLM component connector. Similarly, the user may select an SIU representation 308 to be provided with an interface designed to facilitate configuring a sensor. Settings for a sensor may include, for example, selecting an HLM component name for the SIU, enabling/disabling the SIU connector, and/or the like.

As shown, embodiments of the HLM system mapping Ul 300 may include any number of different types of information, some or all of which may be associated with one or more of the HLM component connector representations. For example, as shown in FIG. 3, the HLM component connector representation 302 may include an indication 314 that the roller pump setting has been selected for that HLM component, an indication 316 of the identification color that has been selected, and/or the like. According to embodiments, the HLM system mapping Ul 300 and/or a Ul accessible therefrom may be configured to present one or more representations of dependencies such as, for example, sensor allocations that have been made, links between pumps, master/slave relationships, and/or the like.

The illustrative HLM system mapping Ul 300 shown in FIG. 3 is not intended to suggest any limitation as to the scope of use or functionality of embodiments of the present disclosure. The illustrative system mapping Ul 300 also should not be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The invention claimed is:

1. A heart lung machine (HLM), comprising:
an HLM base;
a plurality of HLM component connectors coupled to the HLM base, wherein each of the plurality of HLM component connectors comprises a fluid connection element, an energy connection element, and a data connection element configured to facilitate removably connecting a physical HLM component to the HLM base, wherein the physical HLM component comprises one of: a blood pump, an oxygenator, a venous reservoir, an electronic venous occluder, or a sensor that performs an extracorporeal circulation function;

a control assembly comprising a control display device and a processing unit, the processing unit configured to create a mapping profile by:

detecting connections of a plurality of physical HLM components to the plurality of HLM component connectors;

determining that all required physical HLM components for a selected HLM configuration are connected to corresponding HLM component connectors;

initiating, in response to determining that all required physical HLM components are connected, creation of the mapping profile by:

associating each of a plurality of HLM component names with one of a plurality of HLM component roles, wherein each of the plurality of HLM component roles defines an extracorporeal circulation function performed by the corresponding physical HLM component during operation of the HLM;

assigning at least one dependency between a first physical HLM component and a second physical HLM component, the at least one dependency comprising a functional relationship that causes an operational change in the second physical HLM component based on an operational state of the first physical HLM component, wherein the functional relationship comprises at least one of: an interaction, an interaction protocol, and a rule;

providing an HLM system mapping user interface (UI) on a display device, the HLM system mapping UI comprising a plurality of HLM component connector representations, each of the HLM component connector representations corresponding to an HLM component connector;

receiving an indication of a user selection of a first HLM component connector representation of the plurality of HLM component connector representations, the first HLM component connector representation corresponding to a first HLM component connector, wherein the first HLM component connector is configured to facilitate connecting the first physical HLM component to the HLM base;

providing a first HLM component connection mapping interface, the first HLM component connection mapping interface corresponding to the first HLM component connector;

receiving, via the first HLM component connection mapping interface, a user input assigning a first HLM component name to the first physical HLM component; and associating, in response to receiving the user input, the first HLM component name with the first physical HLM component, thereby instantiating the at least one dependency between the first and second physical HLM components.

2. The HLM of claim 1, wherein the processing unit is further configured to receive an indication of a system mapping trigger event and provide the HLM system mapping UI in response to receiving the indication of the system mapping trigger event, wherein the system mapping trigger event comprises detection of connection of a physical HLM component to an HLM component connector.

3. The HLM of claim 2, wherein the system mapping trigger event comprises a detection of a connection of each physical HLM component to the plurality of HLM component connectors.

4. The HLM of claim 1, wherein the processing unit is further configured to provide a name list comprising the first HLM component name, wherein the processing unit populates the name list with the first HLM component name based on a control functionality of a first actuator control unit (ACU) that controls operation of the physical HLM component, wherein the first ACU determines the control functionality by detecting an actuator type of the first physical HLM component.

5. The HLM of claim 4, wherein the processing unit is further configured to:

determine that the first HLM component name and a second HLM component name are identical; and assign a modifier to the second HLM component name so that the second HLM component name is different than the first HLM component name.

6. The HLM of claim 1, wherein the first HLM component connector comprises a first Sensor Interface Unit (SIU) configured to facilitate connecting a sensor probe to the HLM base.

7. The HLM of claim 6, wherein an additional HLM component connector comprises an additional Sensor Interface Unit (SIU) configured to facilitate connecting an additional sensor probe to the HLM base, wherein the processing unit is further configured to:

associate, in response to a first user input, a first sensor name with the first SIU;

associate, in response to a second user input, a second sensor name with the additional SIU; and associate a virtual sensor name with a virtual sensor SIU, the virtual sensor SIU representing a relationship between the first SIU and the additional SIU.

8. The HLM of claim 1, wherein the at least one dependency comprises the rule, wherein the rule comprises at least one of: an intervention that stops pump operation upon air detection, a stop link that adjusts cardioplegia pump speed based on arterial pump speed, and a master/slave relationship that maintains a predefined flow ratio between pumps.

9. The HLM of claim 1, wherein the processing unit is further configured to present, on the display device, a representation of the at least one dependency.

10. The HLM of claim 1, wherein the processing unit is further configured to provide a list of the plurality of HLM component names via the display device.

11. The HLM of claim 1, wherein the processing unit is further configured to facilitate creating an additional mapping profile and saving the mapping profile and the additional mapping profile in a memory.

12. A method of using a heart lung machine (HLM), the HLM comprising an HLM base and a plurality of HLM component connectors coupled to the HLM base, wherein each of the plurality of HLM component connectors comprises fluid connection elements, energy connection elements, and data connection elements configured to facilitate removably connecting physical HLM components to the base, the method comprising:

detecting connections of a plurality of physical HLM components to the plurality of HLM component connectors;

determining that all required physical HLM components for a selected HLM configuration are connected to corresponding HLM component connectors;

initiating, in response to determining that all required physical HLM components are connected, creation of the mapping profile by:

associating each of a plurality of HLM component names with one of a plurality of HLM component roles, wherein each of the plurality of HLM component roles defines an extracorporeal circulation function performed by the corresponding physical HLM component during operation of the HLM, wherein the physical HLM component comprises one of: a blood pump, an oxygenator, a venous reservoir, an electronic venous occluder, or a sensor;

assigning at least one dependency between a first physical HLM component and a second physical HLM component, the at least one dependency comprising a functional relationship that causes an operational change in the second physical HLM component based on an operational state of the first physical HLM component, wherein the functional relationship comprises at least one of; an interaction, an interaction protocol, and a rule;

receiving an indication of a system mapping trigger event;

providing, in response to receiving the indication of the system mapping trigger event, an HLM system mapping user interface (UI) on a display device, the HLM system mapping UI comprising a plurality of HLM component connector representations, each of the HLM component connector representations corresponding to an HLM component connector;

receiving a first indication of a user selection of a first HLM component connector representation, the first HLM component connector representation corresponding to a first HLM component connector, wherein the first HLM component connector is configured to facilitate connecting the first physical HLM component to the HLM base;

providing a first HLM component connector mapping interface, the first HLM component connector mapping interface corresponding to the first HLM component connector;

receiving, via the first HLM component connector mapping interface, a first user input assigning a first HLM component name to the first HLM component connector;

associating, in response to receiving the first user input, the first HLM component name with the first physical HLM component;

receiving a second indication of a user selection of a second HLM component connector representation, the second HLM component connector representation corresponding to a second HLM component connector, wherein the second HLM component connector is configured to facilitate connecting the second physical HLM component to the HLM base;

providing a second HLM component connector mapping interface, the second HLM component connector mapping interface corresponding to the second HLM component connector;

receiving, via the second HLM component connector mapping interface, a second user input assigning a second HLM component name to the second HLM component connector; and associating, in response to receiving the second user input, the second HLM component name with the second physical HLM component.

13. The method of claim 12, further comprising populating a name list with the first HLM component name based on a control functionality of a first actuator control unit (ACU), wherein the first ACU determines the control functionality by detecting an actuator type of the connected physical HLM component, and causing the name list to be presented to a user.

14. The method of claim 13, further comprising:
determining that the first HLM component name and a second HLM component name are identical; and
assigning a modifier to the second HLM component name so that the second HLM component name is different than the first HLM component name.

15. The method of claim 12, wherein the first HLM component connector comprises a first Sensor Interface Unit (SIU) configured to facilitate connecting a first sensor probe to the HLM base.

16. The method of claim 15, wherein the second HLM component connector comprises a second Sensor Interface Unit (SIU) configured to facilitate connecting a second sensor probe to the HLM base, the method further comprising:
associating, in response to a first user input, a first sensor name with the first SIU;
associating, in response to a second user input, a second sensor name with a second sensor SIU; and
associating a virtual sensor name with a virtual sensor SIU, the virtual sensor SIU representing a relationship between the first sensor SIU and the second sensor SIU.

17. The method of claim 12, wherein the at least one dependency comprises the rule, wherein the rule comprises at least one of; an intervention that stops pump operation upon air detection, a stop link that adjusts cardioplegia pump speed based on arterial pump speed, and a master/slave relationship that maintains a predefined flow ratio between pumps.

18. The method of claim 12, wherein the system mapping trigger event comprises detection of a connection of a physical HLM component to a HLM component connector.

19. The method of claim 12, further comprising presenting, on the display device, a representation of the at least one dependency.

20. One or more non-transitory computer-readable media having computer executable instructions embodied thereon that are configured to cause a processing unit, upon being executed by the processing unit, to perform a method of using a heart lung machine (HLM), the HLM comprising an HLM base and a plurality of component connections coupled to the HLM base, wherein each of the plurality of component connections comprises fluid connection elements, energy connection elements, and data connection elements configured to facilitate removably connecting a physical HLM component to the base, the method comprising:

detecting connections of a plurality of physical HLM components to the plurality of HLM component connectors;

determining that all required physical HLM components for a selected HLM configuration are connected to corresponding HLM component connectors;

initiating, in response to determining that all required physical HLM components are connected, creation of the mapping profile by:

associating each of a plurality of HLM component names with one of a plurality of HLM component roles, wherein each of the plurality of HLM component roles defines an extracorporeal circulation function performed by the corresponding physical HLM component during operation of the HLM, wherein the physical HLM component comprises one of: a blood pump, an oxygenator, a venous reservoir, an electronic venous occluder, or a sensor;

assigning at least one dependency between a first physical HLM component and a second physical HLM component, the at least one dependency comprising a functional relationship that causes an operational change in the second physical HLM component based on an operational state of the first physical HLM component, wherein the functional relationship comprises at least one of: an interaction, an interaction protocol, and a rule;

providing an HLM system mapping user interface (UI) on a display device, the HLM system mapping UI comprising a plurality of HLM component connection representations, each of the HLM component connection representations corresponding to an HLM component connection;

receiving an indication of a user selection of a first HLM component connection representation of the plurality of HLM component connection representations, the first HLM component connection representation corresponding to a first HLM component connection, wherein the first HLM component connection is configured to facilitate connecting the first physical HLM component to the HLM base;

providing a first HLM component connection mapping interface, the first HLM component connection mapping interface corresponding to the first HLM component connection;

receiving, via the first HLM component connection mapping interface, a first user input assigning a first HLM component name to the first physical HLM component; and associating, in response to receiving the first user input, the first HLM component name with the first physical HLM component.

\* \* \* \* \*